US010302597B2

(12) United States Patent
Hermann

(10) Patent No.: US 10,302,597 B2
(45) Date of Patent: May 28, 2019

(54) ACOUSTIC PROFILE RECOGNITION FOR DISCRIMINATING BETWEEN HAZARDOUS EMISSIONS AND NON-HAZARDOUS EMISSIONS

(71) Applicant: Carrier Corporation, Farmington, CT (US)

(72) Inventor: Theodore Hermann, Eden Praire, MN (US)

(73) Assignee: CARRIER CORPORATION, Farmington, CT (US)

( * ) Notice: Subject to any disclaimer, the term of this patent is extended or adjusted under 35 U.S.C. 154(b) by 266 days.

(21) Appl. No.: 15/285,718

(22) Filed: Oct. 5, 2016

(65) Prior Publication Data
US 2017/0102365 A1 Apr. 13, 2017

Related U.S. Application Data

(60) Provisional application No. 62/238,884, filed on Oct. 8, 2015.

(51) Int. Cl.
G01N 29/14 (2006.01)
G01N 29/22 (2006.01)
(Continued)

(52) U.S. Cl.
CPC .......... G01N 29/14 (2013.01); G01M 3/007 (2013.01); G01M 3/243 (2013.01); G01N 29/032 (2013.01); G01N 29/227 (2013.01); G01N 29/30 (2013.01); G01N 29/42 (2013.01); G01N 29/4427 (2013.01); G01N 29/4436 (2013.01); G01N 29/4445 (2013.01);
(Continued)

(58) Field of Classification Search
None
See application file for complete search history.

(56) References Cited

U.S. PATENT DOCUMENTS 4,046,220 A   9/1977   Glenn, Jr.
4,960,079 A   10/1990  Marziale et al.
(Continued)

FOREIGN PATENT DOCUMENTS

| CA | 2337000 A1 | 1/2000 |
| CN | 102494247 A | 6/2012 |
| JP | 2002180116 A | 6/2002 |

OTHER PUBLICATIONS

Detronics, "Instructions, FlexSonic Acoustic Detector AC100 Sensor ATX10 Transmitter", Detector Electronics Corporation 2013, Rev: Jun. 2013, 95/8657, 37 pages.
(Continued)

Primary Examiner — Paul M. West
Assistant Examiner — Mark A Shabman
(74) Attorney, Agent, or Firm — Cantor Colburn LLP

(57) ABSTRACT

A method for classifying an emission includes generating a first acoustic profile at a first acoustic sensor; generating a second acoustic profile at a second acoustic sensor; comparing the first acoustic profile to a first reference acoustic profile to generate a first difference; comparing the second acoustic profile to a second reference acoustic profile to generate a second difference; and classifying the emission as one of a hazardous emission or a non-hazardous emission in response to the first difference and the second difference.

15 Claims, 4 Drawing Sheets

(51) Int. Cl.
  *G01N 29/30* (2006.01)
  *G01N 29/42* (2006.01)
  *G01M 3/00* (2006.01)
  *G01M 3/24* (2006.01)
  *G01N 29/032* (2006.01)
  *G01N 29/44* (2006.01)
  *G01N 29/48* (2006.01)

(52) U.S. Cl.
  CPC ......... *G01N 29/4454* (2013.01); *G01N 29/48* (2013.01); *G01N 2291/015* (2013.01); *G01N 2291/021* (2013.01)

(56) References Cited

U.S. PATENT DOCUMENTS

| | | | |
|---|---|---|---|
| 5,416,724 A | 5/1995 | Savic | |
| 5,535,136 A | 7/1996 | Standifer | |
| 5,650,943 A | 7/1997 | Powell et al. | |
| 6,389,881 B1 | 5/2002 | Yang et al. | |
| 6,507,790 B1 | 1/2003 | Radomski | |
| 6,668,619 B2 | 12/2003 | Yang et al. | |
| 6,725,705 B1 | 4/2004 | Huebler et al. | |
| 7,318,335 B2 | 1/2008 | Olesen et al. | |
| 7,607,351 B2* | 10/2009 | Allison | F16L 55/00 702/36 |
| 7,940,189 B2 | 5/2011 | Brown | |
| 8,533,131 B2 | 9/2013 | Hoege | |
| 8,955,383 B2 | 2/2015 | Huseynov et al. | |
| 8,964,509 B2 | 2/2015 | Hermann | |
| 2010/0268489 A1 | 10/2010 | Lie et al. | |
| 2013/0030577 A1* | 1/2013 | Jarrell | F17D 5/00 700/282 |
| 2014/0005958 A1 | 1/2014 | Baliga | |
| 2014/0121999 A1 | 5/2014 | Bracken et al. | |
| 2015/0002300 A1 | 1/2015 | Cho et al. | |

OTHER PUBLICATIONS

General Monitors, "Observer-i, Ultrasonic Gas Leak Detector" accessed Oct. 5, 2016, available at http://s7d9.scene7.com/is/content/minesafetyappliances/Gassonic%20Observer-i%20Data%20Sheet_EN, 2 pages.
European Search Report for application EP 16190220.0, dated Dec. 22, 2016, 8 pages.
European Office Action for application EP 16190220.0, dated Jun. 21, 2018, 13 pages.
Mostafapour et al., "Analysis of leakage in high pressure pipe using acoustic emission method", Applied Acoustics 74 (2013), pp. 335-342.

* cited by examiner

ACOUSTIC PROFILE RECOGNITION FOR DISCRIMINATING BETWEEN HAZARDOUS EMISSIONS AND NON-HAZARDOUS EMISSIONS

CROSS-REFERENCE TO RELATED APPLICATIONS

This application claims the benefit of U.S. provisional patent application Ser. No. 62/238,884 filed Oct. 8, 2015, the entire contents of which are incorporated herein by reference.

BACKGROUND

The present disclosure relates generally to leak detection, and in particular, to use of acoustic profile recognition in discriminating between hazardous emissions and non-hazardous emissions.

Acoustic technology for detection of leaks (e.g., gas leaks) in hazardous locations has been commercially available for over a decade. Much of the advancement with acoustic leak detection has been focused on discriminating between an actual gas leak and potential false sources of acoustic noise in the frequency range of interest (e.g., ultrasonic frequencies). While conventional acoustic detection can provide very good discrimination between pressurized gas leaks and false positives, there is a real and un-met industry need to provide discrimination between hazardous emissions and non-hazardous emissions. A non-hazardous emission may be an escape of pressurized gas that occurs during normal plant operations or as part of maintenance, start-up, or shut down procedures. Sources of non-hazardous emission can be overpressure valves, flare stacks, shop air and emergency shutdown release. These non-hazardous emissions are actual pressurized gas escapes, can be very large in magnitude, and will be detected as an alarm condition by conventional acoustic detectors. Ideally, an acoustic detector would be able to distinguish between hazardous and non-hazardous emissions, however common practice is to either increase the alarm threshold, or physically move the detector away from the source of the non-hazardous emission to avoid an alarm. Both of these practices de-sensitize the detector to hazardous emissions in the same vicinity. Also, some of the non-hazardous emissions can be of significant duration, making the adjustment to a longer alarm time threshold impractical.

SUMMARY

In one embodiment, a method for classifying an emission includes generating a first acoustic profile at a first acoustic sensor; generating a second acoustic profile at a second acoustic sensor; comparing the first acoustic profile to a first reference acoustic profile to generate a first difference; comparing the second acoustic profile to a second reference acoustic profile to generate a second difference; and classifying the emission as one of a hazardous emission or a non-hazardous emission in response to the first difference and the second difference.

In addition to one or more of the features described above, or as an alternative, further embodiments may include, wherein the first acoustic profile comprises measured sound pressure levels across a plurality of frequencies.

In addition to one or more of the features described above, or as an alternative, further embodiments may include, wherein the first difference comprises a root mean square error.

In addition to one or more of the features described above, or as an alternative, further embodiments may include, wherein the emission is determined to be hazardous if either (i) the first difference is greater than a first threshold or (ii) the second difference is greater than a second threshold.

In addition to one or more of the features described above, or as an alternative, further embodiments may include, wherein the gas emission is determined to be non-hazardous if both (i) the first difference is less than a first threshold and (ii) the second difference is less than a second threshold.

In addition to one or more of the features described above, or as an alternative, further embodiments may include, wherein the first threshold and the second threshold are the same.

In addition to one or more of the features described above, or as an alternative, further embodiments may include, wherein generating the first difference occurs at the first acoustic sensor.

In addition to one or more of the features described above, or as an alternative, further embodiments may include, wherein the first acoustic sensor transmits the first difference to a controller.

In addition to one or more of the features described above, or as an alternative, further embodiments may include, wherein generating the second difference occurs at the second acoustic sensor.

In addition to one or more of the features described above, or as an alternative, further embodiments may include, wherein the second acoustic sensor transmits the second difference to a controller.

In another embodiment, a system for classifying an emission includes a first acoustic sensor to generate a first acoustic profile; a second acoustic sensor to generate a second acoustic profile; a controller in communication with the first acoustic sensor and the second acoustic sensor over a network; the controller classifying the emission as one of a hazardous emission or a non-hazardous emission in response to a first difference between the first acoustic profile and a first reference acoustic profile and a second difference between the second acoustic profile and a second reference acoustic profile.

In addition to one or more of the features described above, or as an alternative, further embodiments may include, wherein the first acoustic sensor generates the first difference and transmits the first difference to the controller and the second acoustic sensor generates the second difference and transmits the second difference to the controller.

In addition to one or more of the features described above, or as an alternative, further embodiments may include, wherein controller generates the first difference and the second difference.

In addition to one or more of the features described above, or as an alternative, further embodiments may include, wherein the first acoustic profile comprises measured sound pressure levels across a plurality of frequencies.

In addition to one or more of the features described above, or as an alternative, further embodiments may include, wherein the first difference is a root mean square error.

In addition to one or more of the features described above, or as an alternative, further embodiments may include, wherein the emission is determined to be hazardous if either (i) the first difference is greater than a first threshold or (ii) the second difference is greater than a second threshold.

In addition to one or more of the features described above, or as an alternative, further embodiments may include, wherein the gas emission is determined to be non-hazardous if both (i) the first difference is less than a first threshold and (ii) the second difference is less than a second threshold.

In addition to one or more of the features described above, or as an alternative, further embodiments may include, wherein the first threshold and the second threshold are the same.

In addition to one or more of the features described above, or as an alternative, further embodiments may include, wherein the network is a wireless network.

The foregoing features and elements may be combined in various combinations without exclusivity, unless expressly indicated otherwise. These features and elements as well as the operation thereof will become more apparent in light of the following description and the accompanying drawings. However, it should be understood that the following description and drawings are intended to be exemplary in nature and non-limiting.

BRIEF DESCRIPTION OF THE DRAWINGS

Various features will become apparent to those skilled in the art from the following detailed description of the disclosed non-limiting embodiments. The drawings that accompany the detailed description can be briefly described as follows.

DETAILED DESCRIPTION

Figure 1:
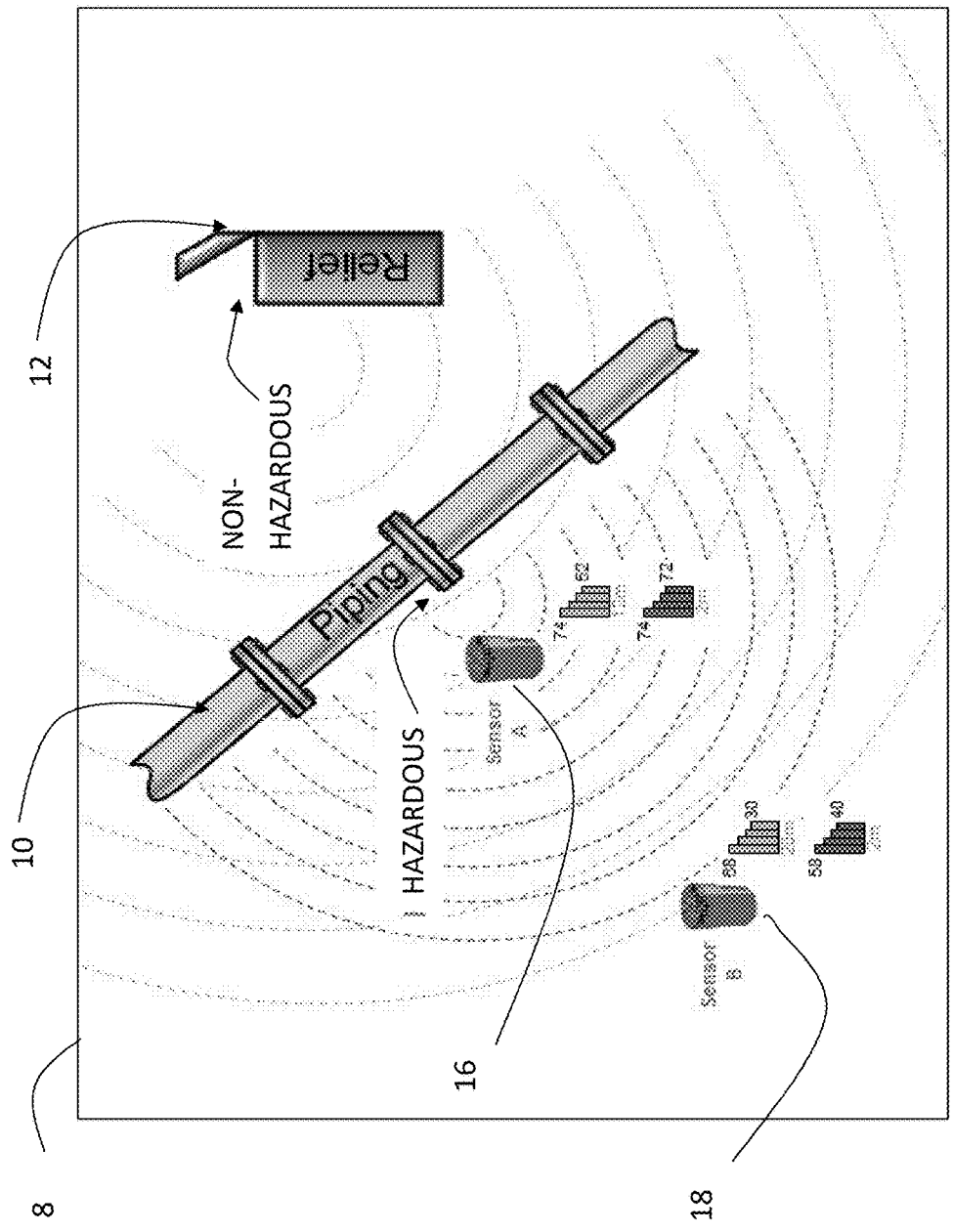
FIG. 1 depicts an environment for implementation of an exemplary embodiment.

FIG. 1 depicts an environment 8 for implementation of an exemplary embodiment. Exemplary embodiments use acoustic sensors to distinguish between a hazardous emission (e.g., a gas leak) and a non-hazardous emission (e.g., gas release at an overpressure relief valve). Shown in FIG. 1 is an exemplary facility including a potential source of a hazardous emission 10. In the example in FIG. 1, the potential source of a hazardous emission 10 is a pipe carrying pressurized gas, but it is understood that potential sources of hazardous emission may include a wide variety of components. Also, shown in FIG. 1 is a source of non-hazardous emission 12. In the example in FIG. 1, the source of a non-hazardous emission 12 is pressure relief valve, but it is understood that potential sources of non-hazardous emission may include a wide variety of components.

Also shown in FIG. 1 are acoustic sensors 16 and 18. A first acoustic sensor 16 is located at a first position and a second acoustic sensor 18 is located at a second position, different from the first position. Although only two acoustic sensors 16/18 are shown in FIG. 1, it is understood that embodiments may utilize any number of acoustic sensors, and embodiments are not limited to two acoustic sensors.

During operation, each acoustic sensor 16/18 continually generates an acoustic profile. The acoustic profile represents sound pressure level (SPL) across a number of frequencies. In an exemplary embodiment, the SPL is measured across frequencies in the ultrasonic range (e.g., 20 kHz to 80 kHz), but it is understood that SPLs may be measured across a different range of frequencies. If the sensed acoustic profile indicates a potential alarm, the sensed acoustic profile is compared to a respective reference acoustic profile to distinguish an emission as either hazardous (e.g., a gas leak) or non-hazardous (e.g., a pressure relief valve).

Figure 2:
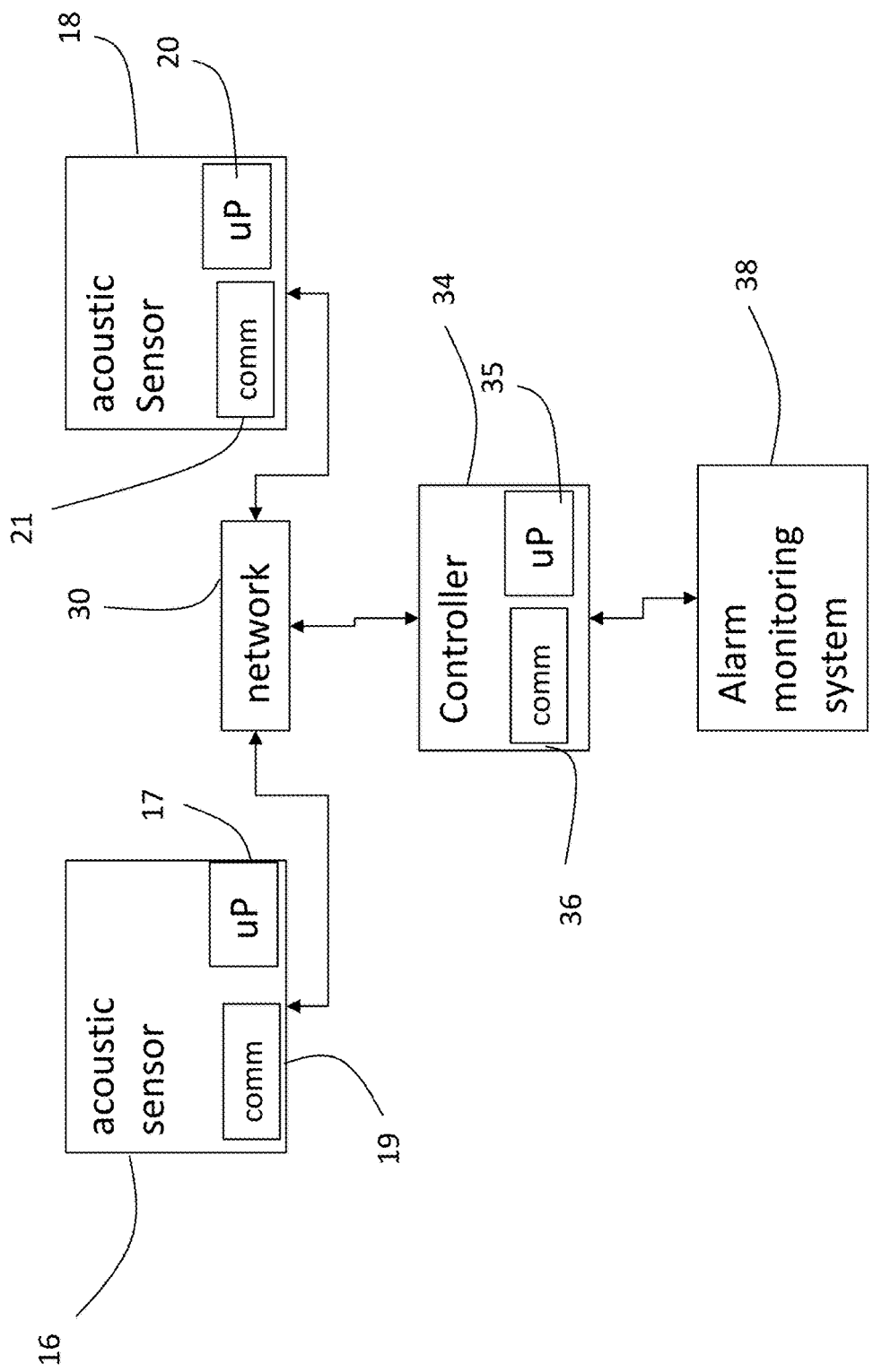
FIG. 2 depicts a system for discriminating between a hazardous emission and a non-hazardous emission in an exemplary embodiment.

FIG. 2 depicts a system for discriminating between a hazardous emission and a non-hazardous emission in an exemplary embodiment. The acoustic sensors 16/18 are shown connected to a network 30. The network 30 may be a wired, wireless, or combination wired/wireless network. The network 30 provides for bidirectional communication between a controller 34 and the acoustic sensors 16/18. Acoustic sensor 16 may include a processor 17 (e.g., a general purpose microprocessor) that performs operations in response to software/firmware stored in a memory. The processor 17 can be any type or combination of computer processors, such as a microprocessor, microcontroller, digital signal processor, application specific integrated circuit, programmable logic device, and/or field programmable gate array. Acoustic sensor 16 also includes a communications interface 19 (e.g., a network card or chip) for enabling communications over network 30. Acoustic sensor 18 may be similarly constructed, and may include a processor 20 and communication interface 21.

The controller 34 may include a processor 35 (e.g., a general purpose microprocessor) that performs operations in response to software/firmware stored in a memory. The processor 35 can be any type or combination of computer processors, such as a microprocessor, microcontroller, digital signal processor, application specific integrated circuit, programmable logic device, and/or field programmable gate array. The controller 34 also includes a communications interface 36 (e.g., a network card or chip) for enabling communications over network 30. The controller 34 interfaces with the acoustic sensors 16/18 and an alarm monitoring system 38. The controller 34 may be in communication with alarm monitoring system 38 over wired connection, wireless connection, or combination wired/wireless connection.

Figure 3:
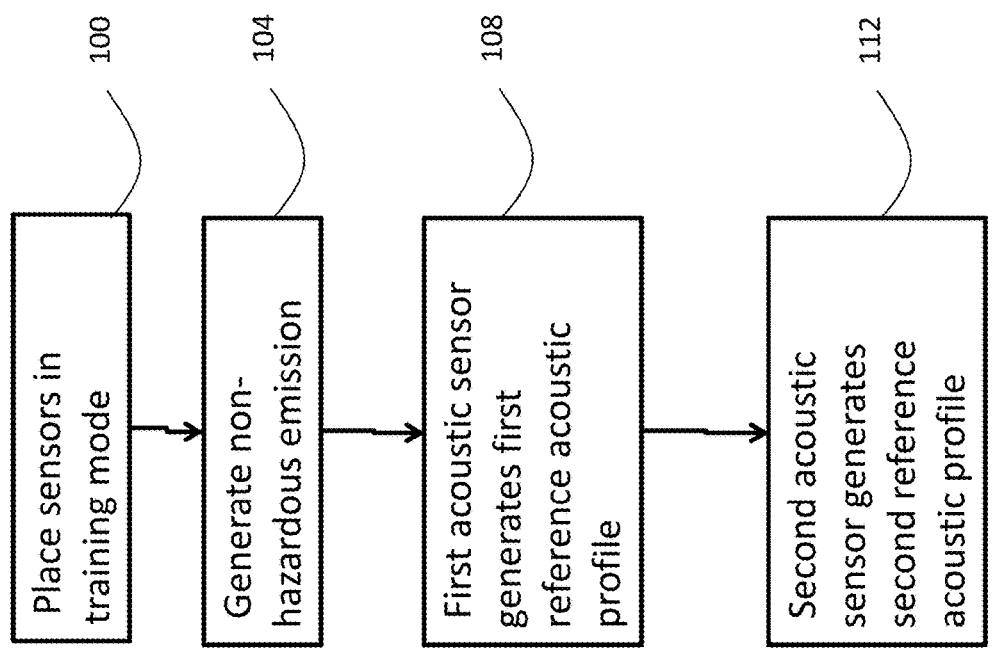
FIG. 3 depicts a method of training acoustic sensors in an exemplary embodiment.

In order to detect non-hazardous emissions in the environment 8, the acoustic sensors 16/18 are operated in a training mode to generate a reference acoustic profile for one or more sources of non-hazardous emission. FIG. 3 depicts a method of training the acoustic sensors 16/18 in an exemplary embodiment. The training is performed to generate a reference acoustic profile for each non-hazardous emission at each acoustic sensor 16/18. These reference acoustic profiles are then used to discriminate between a hazardous emission and a non-hazardous emission.

The training mode begins at 100, where the acoustic sensors 16/18 are placed in a training mode. This may be performed by controller 34 sending a command to the acoustic sensors 16/18 to enter a training mode. Once the acoustic sensors 16/18 are in training mode, flow proceeds to 104 where the non-hazardous emission is activated. This may include, for example, operating an over-pressure relief valve or other source of non-hazardous emission. At 108, the first acoustic sensor 16 generates a first reference acoustic profile. The first reference acoustic profile includes the SPLs sensed across a plurality of frequencies in response to the non-hazardous emission. The first reference acoustic profile may be stored in the acoustic sensor 16 and/or transmitted to the controller 34. At 112, the second acoustic sensor 18 generates a second reference acoustic profile. The second reference acoustic profile includes the SPLs sensed across a plurality of frequencies in response to the non-hazardous emission. The second reference acoustic profile may be stored in the acoustic sensor 18 and/or transmitted to the controller 34.

Figure 4:
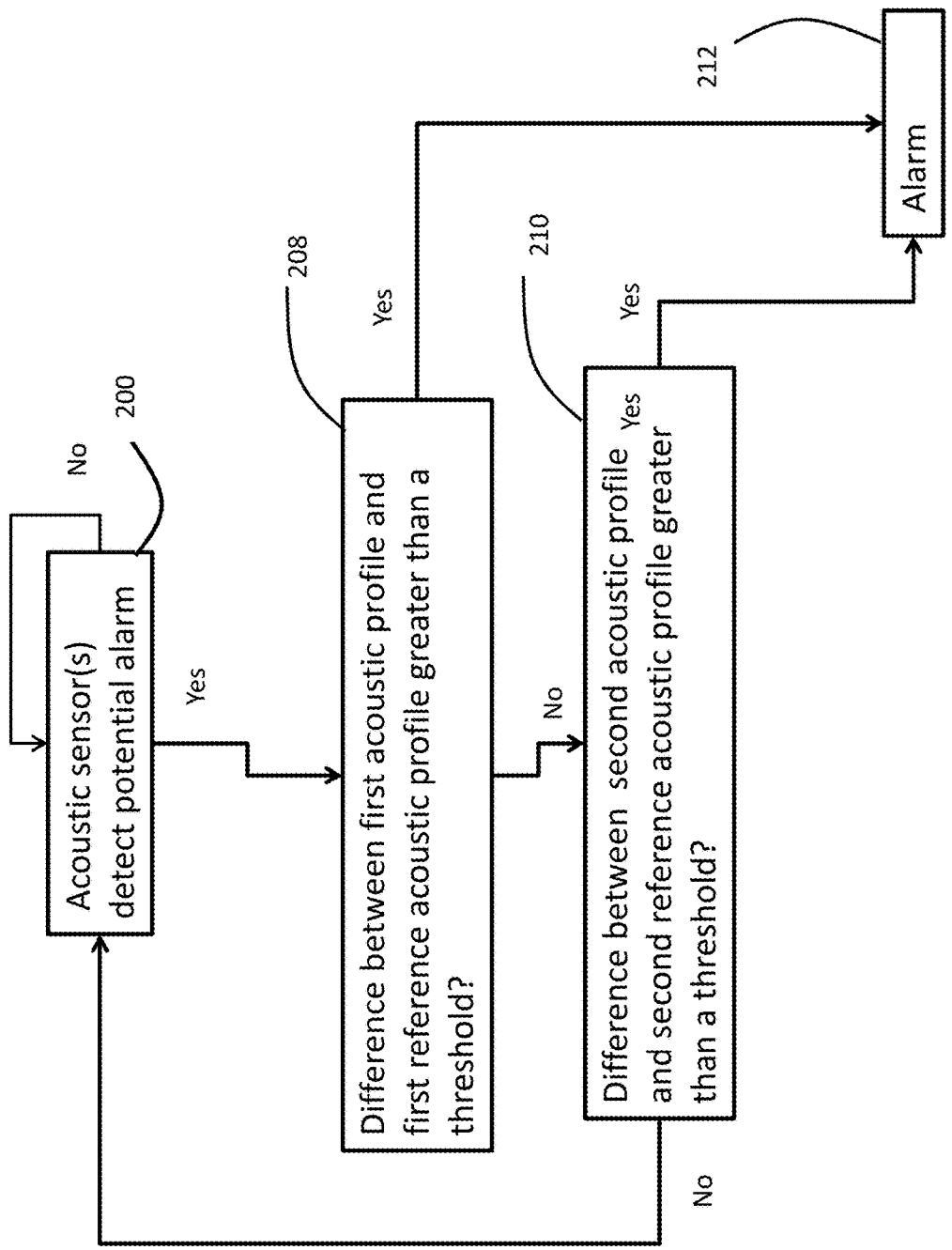
FIG. 4 depicts a method of discriminating between a hazardous emission and a non-hazardous emission in an exemplary embodiment.

FIG. 4 depicts a method of discriminating between a hazardous emission and a non-hazardous emission in an exemplary embodiment. The process begins at 200 where acoustic sensors 16/18 operate to detect a potential alarm. A potential alarm may be detected when one or both of the acoustic sensors 16/18 detect an SPL that is above the SPL of the normal background noise of the environment 8 by some amount. The acoustic sensors 16/18 continually monitor the environment 8, and thus continually generate acoustic profiles. In an exemplary embodiment, each acoustic sensor 16/18 monitors a plurality of frequency bands. If a predetermined number of frequency bands (e.g., 14 out of 24) have exceeded the normal background noise by some dB, then a potential leak is indicated.

If a potential alarm is present, then at 208 a first acoustic profile from first acoustic sensor 16 is compared to the first reference acoustic profile to determine if a first difference between the first acoustic profile and the first reference acoustic profile is greater than a threshold. In an exemplary embodiment, the first acoustic profile is compared to the first reference acoustic profile using a root mean-square error (MSE) technique. It is understood that other techniques for comparing the acoustic profiles may be used. At 208, if the first difference exceeds a threshold (e.g., 6 db) then flow proceeds to 212, where the emission is classified as hazardous and an alarm condition is generated.

With a negative outcome at 208, flow proceeds to 210 where the second acoustic profile is compared to the second reference acoustic profile to determine if a second difference between the second acoustic profile and the second reference acoustic profile is greater than a threshold. In an exemplary embodiment, the second acoustic profile is compared to the second reference acoustic profile using a root mean-square error (MSE) technique. It is understood that other techniques for comparing the acoustic profiles may be used. At 210, if the second difference exceeds a threshold (e.g., 6 db) then flow proceeds to 212, where the emission is classified as hazardous and an alarm condition is generated. The threshold used at 208 may be the same or different than the threshold used at 210. With a negative outcome at 210, flow proceeds back to 200. Thus, if both the first difference and the second difference are less than the respective thresholds, then an alarm condition is not indicated as the source of the emission is classified as non-hazardous.

FIG. 4 illustrates generating an alarm condition if either of the first difference or the second difference is greater than a threshold. If 3 or more acoustic sensors are used, then different logic may be used to determine an alarm condition. In one embodiment, the differences between the respective acoustic profiles and reference acoustic profiles must be less than a threshold for all acoustic sensors to avoid an alarm condition. In another embodiment, the differences between the respective acoustic profiles and reference acoustic profiles must be less than a threshold for a majority of the acoustic sensors to avoid an alarm condition. Furthermore, individual acoustic sensor thresholds may be adjusted up/down based on the real-time signal strength of the real time acoustic SPL. For example, sensors closer to background noise may be assigned more error margin, or a larger threshold.

Operations 208 and 210 may be performed at either acoustic sensors 16/18 or at the controller 34. In one embodiment, the acoustic sensor 16 stores the first reference acoustic profile and the acoustic sensor 18 stores the second reference acoustic profile. In operation, the comparison at 208 between the first acoustic profile and the first reference acoustic profile is performed by acoustic sensor 16. The acoustic sensor 16 then transmits an alarm code and the result of the comparison to the controller 34. The controller 34 can then distinguish between a hazardous emission and a non-hazardous emission based on the difference between the between the first acoustic profile and the first reference acoustic profile. Similarly, the comparison at 210 between the second acoustic profile and the second reference acoustic profile may be performed by acoustic sensor 18.

If either acoustic sensor 16 or acoustic sensor 18 senses an alarm condition, an alarm signal is provided to the controller 34 along with the result of the comparison at operations 208 and 210 (e.g., the difference in db). The controller may actively poll acoustic sensors 16/18 for the difference values upon receiving a potential alarm condition. This reduces the amount of data transmitted on the network 30, as the acoustic sensors 16/18 only transmit the presence of a potential alarm condition and the result of the comparison to the reference acoustic profile, and not the full acoustic profiles.

In other embodiments, the controller 34 stores the first reference acoustic profile and the second reference acoustic profile. The acoustic sensors 16/18 transmit the sensed first and second acoustic profiles to the controller 34. Controller 34 then performs operations 208 and 210. Regardless of which device performs operations 208 and 210, the controller 34 may communicate an alarm condition to the alarm monitoring system 38.

In the embodiments described herein, only two acoustic sensors 16/18 are shown, but it is understood that embodiments may use a higher number of acoustic sensors throughout the environment 8. Each acoustic sensor may store multiple reference acoustic profiles corresponding to multiple sources of non-hazardous emissions.

Embodiments allow for detection of non-hazardous emissions while still maintaining maximum sensitivity. Embodiments discriminate between hazardous emissions and non-hazardous emissions without compromising detector sensitivity. The system may be customized to each environment using the training mode and new source of non-hazardous emissions can be added at any time to an existing installation through additional training. Low bandwidth communication between the acoustic sensors 16/18 and the controller 34 allows for use of a simple wireless network 30. Using multiple acoustic sensors allows for identifying direction and/or location of hazardous emissions. Acoustic sensors 16/18 generate unique reference acoustic profiles, which take into account frequency dependent attenuation through the atmosphere. In this manner, the two acoustic sensors are able to distinguish between emissions of varying amplitudes and locations that could mimic a non-hazardous emission.

While the present disclosure is described with reference to exemplary embodiments, it will be understood by those skilled in the art that various changes may be made and equivalents may be substituted without departing from the spirit and scope of the present disclosure. In addition, various modifications may be applied to adapt the teachings of the present disclosure to particular situations, applications, and/or materials, without departing from the essential scope thereof. The present disclosure is thus not limited to the particular examples disclosed herein, but includes all embodiments falling within the scope of the appended claims.

What is claimed is:

1. A method for classifying an emission, the method comprising:
   generating a first acoustic profile at a first acoustic sensor;
   generating a second acoustic profile at a second acoustic sensor;
   generating a third acoustic profile at a third acoustic sensor;
   comparing the first acoustic profile to a first reference acoustic profile to generate a first difference;
   comparing the second acoustic profile to a second reference acoustic profile to generate a second difference;
   comparing the third acoustic profile to a third reference acoustic profile to generate a third difference; and
   classifying the emission as a non-hazardous emission when (i) the first difference is greater than a first threshold (ii) the second difference is less than a second threshold and (iii) the third difference is less than a third threshold.

2. The method of claim 1 wherein the first acoustic profile comprises measured sound pressure levels across a plurality of frequencies.

3. The method of claim 1 wherein the first difference comprises a root mean square error.

4. The method of claim 1 wherein the first threshold and the second threshold are the same.

5. The method of claim 1 wherein generating the first difference occurs at the first acoustic sensor.

6. The method of claim 5 wherein the first acoustic sensor transmits the first difference to a controller.

7. The method of claim 1 wherein generating the second difference occurs at the second acoustic sensor.

8. The method of claim 7 wherein the second acoustic sensor transmits the second difference to a controller.

9. A system for classifying an emission, the system comprising:
   a first acoustic sensor to generate a first acoustic profile;
   a second acoustic sensor to generate a second acoustic profile;
   a third acoustic sensor to generate a third acoustic profile;
   a controller in communication with the first acoustic sensor, the second acoustic sensor and the third acoustic sensor over a network;
   the controller classifying the emission as a non-hazardous emission when (i) the first difference is greater than a first threshold (ii) the second difference is less than a second threshold and (iii) the third difference is less than a third threshold.

10. The system of claim 9 wherein the first acoustic sensor generates the first difference and transmits the first difference to the controller and the second acoustic sensor generates the second difference and transmits the second difference to the controller.

11. The system of claim 9 wherein controller generates the first difference and the second difference.

12. The system of claim 9 wherein the first acoustic profile comprises measured sound pressure levels across a plurality of frequencies.

13. The system of claim 9 wherein the first difference is a root mean square error.

14. The system of claim 9 wherein the first threshold and the second threshold are the same.

15. The system of claim 9 wherein the network is a wireless network.

* * * * *